(12) United States Patent
Hill et al.

(10) Patent No.: US 6,436,379 B1
(45) Date of Patent: *Aug. 20, 2002

(54) EMOLLIENT FOR CUTICLE TREATMENT AND DELIVERY SYSTEM THEREFORE

(75) Inventors: John C. Hill, Mesa; Theresa E. Rodriguez, Laveen; James H. Brown, Scottsdale, all of AZ (US)

(73) Assignee: International Flora Technologies Ltd., Gilbert, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/527,935

(22) Filed: Mar. 16, 2000

Related U.S. Application Data

(63) Continuation-in-part of application No. 09/010,736, filed on Jan. 22, 1998, now Pat. No. 6,280,746, which is a continuation-in-part of application No. 08/953,132, filed on Oct. 17, 1997, now Pat. No. 5,968,530.

(51) Int. Cl.[7] ............................. A61K 6/00; A61K 7/00; A61K 7/04
(52) U.S. Cl. ........................ 424/61; 424/401; 514/873
(58) Field of Search .................... 424/401, 61; 514/873

(56) References Cited

U.S. PATENT DOCUMENTS

| | | | |
|---|---|---|---|
| 4,530,828 A | 7/1985 | Smith et al. | 424/61 |
| 5,034,215 A | 7/1991 | Santa-Coloma Roth | 424/61 |
| RE36,253 E | 7/1999 | DiMeglio | 424/195.1 |
| 5,968,530 A | * 10/1999 | Arquette | 424/401 |

\* cited by examiner

Primary Examiner—Thurman K. Page
Assistant Examiner—S. Howard
(74) Attorney, Agent, or Firm—The Halvorson Law Firm

(57) ABSTRACT

A product for treating and conditioning cuticles using a semi-solid emollient and a complimentary delivery system is disclosed. The emollient could be any semi-solid emollient suitable for cuticle treatment, the emollient preferably including naturally derived botanicals that impart a "dry" feel, and a soothing and softening effect on the cuticle area. Isopropyl jojoba (IPJ) and hydrogenated isopropyl jojoba (HIPJ) esters, hydrogenated jojoba alcohol, jojoba esters, hydrogenated jojoba oil, ethyl macadamiate and other esters, waxes and oils may be used in the emollient to contribute to the "dry" feel and serve as carriers for active materials used to treat cuticles. The semi-solid emollient is retained in a container, preferably in stick form, and is extendable from and preferably retractable into the container, which can be carried by an individual. The container is designed to enable a user to apply the emollient to a cuticle area without touching the emollient with his/her fingertips, thereby preventing application or migration of the emollient to unselected areas.

31 Claims, 3 Drawing Sheets

EMOLLIENT FOR CUTICLE TREATMENT AND DELIVERY SYSTEM THEREFORE

This application is a continuation-in-part of application Ser. No. 09/010,736, filed Jan. 22, 1998 now issued as U.S. Pat. No. 6,280,746, which is a continuation in part of application Ser. No. 08/953,132, filed Oct. 17, 1997 now issued as U.S. Pat. No. 5,968,530.

FIELD OF THE INVENTION

The present invention relates to emollients used to treat cuticles, especially cuticles surrounding finger or toenails. More particularly, the present invention relates to a semi-solid emollient that can be packaged in a container from which the emollient can be extended, and preferably retracted as well.

BACKGROUND

In the field of cosmetic, personal care, and pharmaceutical products, an emollient is defined as an agent that moisturizes and/or softens and/or smoothes the skin. Typically, emollients tend to reduce the roughness, cracking and irritation of the skin. The smoothing is believed to be effected by the penetration of the emollient into the surface layers of tissue.

Emollients tend to be bland, fatty, oleaginous substances. One of the benefits of emollients is their ability to exclude water-soluble irritants, air, and air-borne bacteria. Presently, there are numerous compositions that function as emollients in a wide variety of products, although the respective compositions may function in different ways. For example, certain emollients coat the surface of the skin and serve to impede water loss from the skin. Such emollients are generally comprised of large molecules that form a hydrophobic barrier.

Use of the word "emollient" is often intended to mean a combination of several emollients selected for their individual properties and blended to achieve a desired result. Examples of emollients are lanolin, castor oil, mineral oil, silicone derivatives and petroleum jelly. These products (with the possible exception of the silicone derivatives) typically exhibit an undesirable greasy feel on the skin. Other compositions used as emollients include high oleic sunflower oil and its derivatives, macadamia nut oil and its derivatives, grape seed oil, hazelnut oil, olive oil, sesame oil, and other natural seed and nut oils such as jojoba oil, and derivatives thereof. Of this group the preferred emollients for cosmetic and personal care formulation use are high oleic sunflower oil and its derivatives, macadamia nut oil and its derivatives, and jojoba oil and its derivatives. These emollients are preferred due to their skin feel (they are non-oily and tend to penetrate the skin) and superior oxidative stability when incorporated in cosmetic, pharmaceutical and personal care formulations. Finally, other compositions used as emollients include corn oil, cottonseed oil, rose water ointment, apricot kernel oil, avocado oil, theobroma oil, almond oil, and myristyl alcohol.

Additionally, a number of fatty acids derived from either plants or animal sources have been used as emollients. Fatty acids generally comprise aliphatic hydrocarbon or other organic chains with carboxylic substituents on them, typically having between 8 and 24 carbon atoms in the chain backbone. Fatty acids are often used as emollients or "superfatting agents" (this term being known to those skilled in the art) in creams, lotions, shaving creams, lipsticks and as binding agents in pressed powders and blushes. Fatty acids used in cosmetic formulations include stearic acid, oleic acid, myristic acid and palmitic acid. Other typical fatty acids include linoleic acid, behenic acid, and palmitoleic acid.

Fatty alcohols are also used as emollients. They are said to be less sticky and less heavy than some other fatty materials, such as the fatty acids, and are frequently used to lower the viscosity and improve the stability of lotions and creams. Fatty alcohols are also used in reactive hair dying and perming products. Examples of fatty alcohols used as emollients are lauryl alcohol, cetyl alcohol, stearyl alcohol, jojoba alcohol and oleyl alcohol.

Further, fatty esters are used as emollients. One benefit of fatty esters is that they are not as oily to the touch as some other types of fatty emollients. Examples of fatty esters include isopropyl palmitate, isopropyl myristate and glyceryl stearate. Another fatty ester emollient is ojoba oil, which is derived from the seed of the plant species *Simmondsia chinensis*. Jojoba oil and its derivatives have an excellent skin feel (because they are non-oily and penetrating as compared to some other substances) and impart emolliency without a greasy feel. Jojoba oil is composed almost exclusively of wax esters, with little or no triglycerides present. Further, non-biodegradable emollients, such as hydrocarbons or silicones (such as methyl silicones) are known and are used as emollients in cosmetic and personal care preparations.

One of the problems with typical emollients (other than some of the above-described silicone emollients) is that they impart a wet, oily, or greasy feel to the cuticle area being treated (sometimes referred to herein as the "selected area"). Further, typical emollients are often placed on or migrate to unselected areas. As used herein, the term "unselected area" means an area other than the selected area, and includes the fingertips, face, palm, clothes, furniture, and other surfaces not intended for treatment. When an emollient gets on unselected areas it can lead to an uncomfortable feeling and/or undesirable appearance (leaving a heavy coating and/or shine). Often users of cuticle treatment products containing high levels of oily or greasy components experience a migration of the applied oily or greasy components to unselected surfaces which may causes staining of clothing, furniture coverings and other objects contacted by the user.

In pending U.S. patent application Ser. No. 09/010,736, filed Jan. 22, 1998, and U.S. Pat. No. 5,968,530 to Arquette, both of which are owned by the assignee of the present application, there are disclosed emollients that impart a "dry" feel to the user and, unlike silicones, are naturally derived and biodegradable. These emollients include esters produced from jojoba oil or natural organic seed oil. More particularly, these emollients include ethyl and isopropyl jojoba esters or derivatives together with jojoba oil, randomized jojoba oil, partially saturated and randomized jojoba esters, and long chain jojoba alcohols. Furthermore, in pending U.S. patent application Ser. No. 09/329,882 filed Jun. 11, 1999 to Kleiman, also owned by the assignee of the present application, there are disclosed oxidatively stable long chain ethyl ester emollients comprising stabilized ethyl esters of macadamia nut oil and other natural seed oils. The products disclosed in U.S. Pat. No. 5,968,530 and application Ser. No. 09/010/736 to Arquette and U.S. patent application No. Ser. 09/329,882 to Kleiman are known as "dry emollients" due to the feel of dry emolliency imparted when these products are applied to the skin.

Containers normally used to store and carry typical emollients or commercially available cuticle treatment products are not designed to allow application in such a manner as to contribute to a dry emollient feel. Typical containers include small glass bottles of the same general type used for nail polish. These containers come equipped with a small brush for application of the liquid cuticle treatment product to users' cuticles. Such containers often leak or dry up due to broken caps or improper seals and application of the cuticle treatment product is often an unpleasant event due to its free flowing and oily nature. Another less common container for liquid cuticle treatment is similar to a large felt pen, such as a "Magic Marker" in size, shape and in its method of delivery of the cuticle treatment product through a "wick" similar to the writing tip of a marker. One such container is called a "cuticle Nourishing Pen" (NAGELHAUT-PFLEGESTIFT FEUTRE NOURRISSANT), which contains 0.14 FL. OZ. (4 ml net) of cuticle treatment and is sold by ALESSANDRO GmbH Cosmetics D-40764 of Langenfeld Germany. Although it is in some aspects more convenient than the "nail polish" type container for carrying and delivering a cuticle treatment product, the low-viscosity fluid in such a container dries out quickly. Further, only a treatment product of very low viscosity can be delivered through the wick. Such low viscosity products are not capable of functioning as effective emollients or as effective carriers of actives (also called "active ingredients", or "active materials") for cuticle treatment.

Despite the disclosures of the prior art, including emollient compositions chemically formulated to impart a dry feel, there still remains a need for a cuticle treatment product that can be conveniently carried, stored and used, and that enables the emollient to be delivered only to a selected area, thereby reducing the application or migration of the emollient to unselected areas, and assisting in imparting a dry feel.

SUMMARY OF INVENTION

This invention relates to an improved emollient and to a product for the treatment and care of cuticles. The product comprises a container including the emollient, which allows a user to conveniently store and carry the emollient and apply it directly to the selected area without the emollient being inadvertently applied, or migrating, to unselected areas.

An emollient used in the invention may be any semi-solid emollient or combination of emollients used to treat cuticles, such as emollients including hydrocarbons, silicones, waxes, or emollients derived from seed oils. Preferably, the invention utilizes emollients that are naturally derived from seed and/or nut oils to further impart a "dry" feel while providing emolliency and softening the cuticle area. Most preferably the emollient includes saturated and/or unsaturated ethyl and/or isopropyl esters of long-chain fatty acids and alcohols derived from plant seed and/or nut oils. These are biodegradable, naturally derived emollients that have a tactile property described as "dry," because they are non-oily and preferably penetrate the skin. The improved emollient compositions of the invention may be used alone or as carriers for materials that have specific activity. When delivered to the cuticle area by the emollient the actives may impart (1) activity, and/or (2) aesthetics. Examples of such active materials fare antifungal products, essential oils, antioxidants, topical anesthetics, vitamins, hormones, proteins and herbal extracts.

The emollient of the present invention differs from other cuticle-treatment emollients in various ways, including the fact that it is semi-solid. The emollient differs from other semi-solid emollients, such as those used for lip care, in numerous ways, including its different chemical composition, physical properties, the actives it preferably includes, and the more desirable slip characteristics, as explained herein.

The desired effect of imparting a dry feel to the treatment area may be enhanced when an emollient is applied by a controlled-delivery device. Such a device is preferably a container that retains the emollient without allowing it to dry and which delivers its contents to selected treatment areas. The container should (1) be convenient to carry and fit into a purse or pocket, and (2) enable a user to apply emollient on a cuticle without the user having to touch the emollient with his/her fingertips and without said application resulting in the emollient contacting non selected surfaces. Preferably, the container is an extendable/retractable (also called a propel-repel) container, and is most preferably a tube similar to those used for lipcare products. This container delivery device contributes to a perceived dry feel by the user because it (1) facilitates controlled delivery of the emollient to the area selected for treatment, and (2) prevents the emollient from reaching the fingertips of the user, thereby preventing the emollient from migrating to unselected areas, which is undesirable and which can detract from the desired dry emollient feel.

The present invention thus includes a semi-solid emollient for use as a cuticle treatment and a product comprising a semi-solid emollient and a container for storing and delivering the emollient to areas selected for treatment. The emollient is essentially solid at room temperature, and can be provided in various shapes and sizes although it is preferably produced in the shape of a stick or cylinder so that it can be retained in a tube-shaped container.

The novel features that are considered characteristic of the invention are set forth with particularity in the appended claims. The invention itself, however, both as to its structure and its operation together with the additional object and advantages thereof will best be understood from the following description of the preferred embodiment of the present invention when read in conjunction with the accompanying drawings. Unless specifically noted, it is intended that the words and phrases in the specification and claims be given the ordinary and accustomed meaning to those of ordinary skill in the applicable art or arts. If any other meaning is intended, the specification will specifically state that a special meaning is being applied to a word or phrase.

Likewise, the use of the words "function" or "means" in the Description of Preferred Embodiments is not intended to indicate a desire to invoke the special provision of 35 U.S.C. §112, paragraph 6 to define the invention. To the contrary, if the provisions of 35 U.S.C. §112, paragraph 6, are sought to be invoked to define the invention(s), the claims will specifically state the phrases "means for" or "step for" and a function, without also reciting in such phrases any structure, material, or act in support of the function. Even when the claims recite a "means for" or "step for" performing a function, if they also recite any structure, material or acts in support of that means of step, then the intention is not to invoke the provisions of 35 U.S.C. §112, paragraph 6. Moreover, even if the provisions of 35 U.S.C. §112, paragraph 6, are invoked to define the inventions, it is intended that the inventions not be limited only to the specific structure, material or acts that are described in the preferred embodiments, but in addition, include any and all structures, materials or acts that perform the claimed function, along with any and all known or later-developed equivalent structures, materials or acts for performing the claimed function.

DETAILED DESCRIPTION OF PREFERRED EMBODIMENTS

Figure 1:
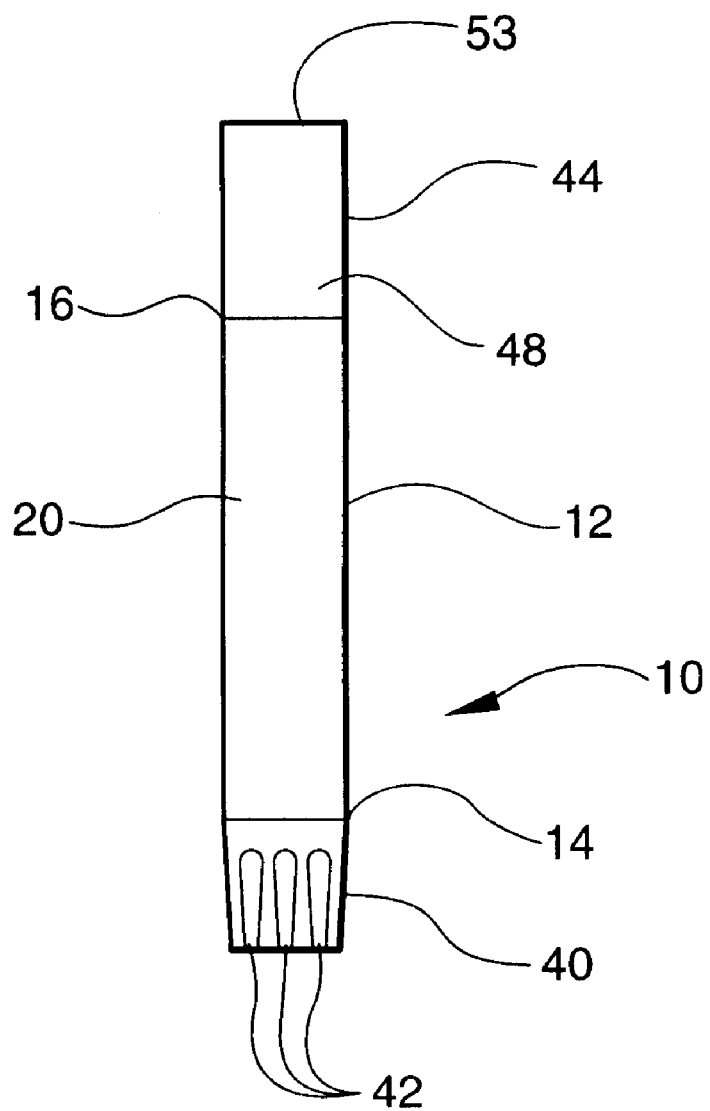
FIG. 1 shows a side view of a preferred container, including a cap, that may be used to retain an emollient according to the invention.

The present invention is a semi-solid emollient that preferably has a low melting point and is preferably isomorphous, used for cuticle treatment, with the emollient preferably being retained in a convenient container, such as a extendable/retractable container, which contributes favorably to the overall consumer impression of dry emolliency. As used herein the terms "extendable/retractable container" or "propel-repel container" refers to any container wherein a semi-solid emollient can (1) be extended for application to a cuticle without touching the emollient with the fingertips, and (2) be retracted into the container without touching it with the fingertips. It is possible, however, that a container according to the invention may only extend the emollient, in which case any emollient outside of the container after application to a cuticle may be covered by a cap or other device, or disposed of in some fashion. Additionally, a container may be used that neither extends or retracts the emollient, but that still enables a user to apply the semi-solid emollient to the selected area.

The emollient may be of any semi-solid composition suitable for cuticle treatment. For example, the emollient may comprise one or more synthetic compositions, such as silicone, or one or more organic compositions such as triglycerides, plant nut or seed oils or one or more of their derivatives. Emollients used in the practice of the invention may include lanolin, castor oil, corn oil, cottonseed oil, rose water ointment, apricot kernel oil, avocado oil, grape seed oil, hazelnut oil, olive oil, sesame oil, theobroma oil, almond oil, myristyl alcohol, fatty acids derived from plant or animal sources, fatty esters and fatty alcohols, high oleic sunflower oil, macadamia nut oil, and other natural seed and nut oils such as jojoba oil, and derivatives thereof. Preferred emollients are disclosed in pending U.S. patent application Ser. No. 09/010,736, filed Jan. 22, 1998, U.S. Pat. No. 5,968,530 to Arquette, and U.S. patent application Ser. No. 09/329,822 filed Jun. 11, 1999 to Kleiman, the respective disclosures of which are incorporated herein by reference. Generally, the above-referenced applications and patent disclose ethyl and isopropyl esters produced from triglyceride oils and jojoba oil derivatives together with jojoba oil, randomized jojoba oil, partially saturated and randomized jojoba esters and long chain jojoba alcohols. Such esters include ethyl macadamiate, isopropyl jojoba (IPJ) and hydrogenated isopropyl jojoba (HIPJ) esters. These emollients impart a "dry emollient" skin feel and at the same time may serve as carriers of active materials for cuticle treatment. These emollients are particularly useful in semi-solid formulations intended for use in cuticle care products.

As used herein, the term "semi-solid" refers to any composition that is of such a consistency that it can properly function at room temperature (68–75 degrees Fahrenheit) when used in a repel-propel container, and is a low melting isomorphous substance. Two examples of preferred cuticle treatment compositions made according to the invention are presented below:

EXAMPLE 1

EXAMPLE 1

| Phase | Trade Name | INCI Name | Supplier | % wt./wt. |
|---|---|---|---|---|
| A. | Floramac 10 | Ethyl Macadamiate | Floratech | 28.90 |
|  | Green Tea Extract w/Florasun 90 | Green Tea Extract (and) Helianthus Annuus (Hybrid Sunflower) Seed Oil | Floratech | 5.00 |
|  | Crystal "O" | Castor Oil | Cas Chem | 29.00 |
|  | Floraesters 30 | Jojoba Esters | Floratech | 7.00 |
|  | Floraesters 70 | Jojoba Esters | Floratech | 3.00 |
|  | Floraesters HIPJ | Hydrogenated Isopropyl Jojobate (and) Hydrogenated Jojoba Alcohol (and) Jojoba Esters | Floratech | 2.00 |
|  | Floraesters IPJ | Isopropyl Jojobate (and) Jojoba Alcohol (and) Jojoba Esters | Floratech | 2.00 |

EXAMPLE 1-continued

| Phase | Trade Name | INCI Name | Supplier | % wt./wt. |
|---|---|---|---|---|
| | Carnauba Wax, Yellow #1 | Copernicia Cerifera (Carnauba) Wax | Strahl & Pitsch | 5.00 |
| | Candelilla Wax | Euphorbia Cerfiera (Candelilla) Wax | Strahl & Pitsch | 7.50 |
| | Yellow Beeswax | Yellow Beeswax | Strahl & Pitsch | 3.00 |
| | Castorwax NF | Hydrogenated Castor Oil | Caschem | 2.00 |
| | Nature Chem CR | Cetyl Ricinoleate | Caschem | 1.60 |
| B. | Ethyl Panthenol | Panthenyl Ethyl Ether | Roche Vitamins | 0.20 |
| | Phytantriol | Phytantriol | Roche Vitamins | 0.20 |
| C. | Phenonip | Phenoxyethanol (and) Methylparaben (and) Butylparaben (and) Ethylparaben (and) Propylparaben | Nipa Hardwicke | 0.60 |
| | Covi-Ox T-70 | Tocopherols | Henkel | 0.10 |
| | Tea Tree Oil | Melaleuca Alternifolia (Tea Tree Oil) Leaf Oil | International Sourcing, Inc. | 1.00 |
| | Vitamin E Acetate | Tocopheryl Acetate | Roche Vitamins | 1.60 |
| | Green Herbal Fragrance | Fragrance | Bell Flavors & Fragrances | 0.30 |
| Total | | — | — | 100.00 |

EXAMPLE 2

EXAMPLE 2

| Phase | Trade Name | INCI Name | Supplier | % wt./wt. |
|---|---|---|---|---|
| A. | Floramac 10 | Ethyl Macadamiate | Floratech | 28.00 |
| | Green Tea Extract | Green Tea Extract (and) Helianthus Annus (Hybrid Sunflower) Seed Oil | Floratech | 5.00 |
| | Castor Oil | Castor Oil | CasChem | 27.00 |
| | Floraesters 30 | Jojoba Esters | Floratech | 7.00 |
| | Floraesters 70 | Jojoba Esters | Floratech | 2.00 |
| | Floraesters HIPJ | Hydrogenated Isopropyl Jojobate (and) Hydrogenated Jojoba Alchohol (and) Jojoba Esters | Floratech | 2.00 |
| | Floraesters IPJ | Isopropyl Jojoba (and) Esters | Floratech | 2.00 |
| | Carnauba Wax, #1 Yellow | Copernicia Cerifera (Carnauba) Wax | Strahl & Pitsch | 5.00 |
| | Candelilia Wax | Euphorbia Cerifera (Candelilla) Wax | Strahl & Pitsch | 7.50 |
| | Yellow Beeswax | Beeswax | Strahl & Pitsch | 3.00 |
| | Castorwax NF | Hydrogenated Castor Oil | CasChem | 2.00 |
| | Nature Chem CR | Cetyl Ricinoleate | CasChem | 1.50 |
| | Michonazole Nitrate | None Assigned (antifungal) | Chemo Iberica S.A. | 2.00 |
| | Tolnaftate | None Assigned (antifungal) | Lusochimica S.P.A. | 1.00 |
| B. | Ethyl Panthenol No. 26100 | Panthenyl Ethyl Ether | Roche Vitamins | 0.20 |
| | Phytantriol | Phytantriol | Roche Vitamins | 0.20 |
| C. | Phenonip | Phenoxyethanol (and) Methylparaben (and) Butylparaben (and) Ethylparaben (and) Propylparaben | Nipa Hardwicke | 0.60 |
| | Covi-Ox T-70 | Tocopherols | Henkel | 0.10 |
| | Tea Tree Oil | Melaleuca Alternifolia (Tea Tree) Leaf Oil | International Sourcing, Inc. | 2.00 |
| | Vitamin E Acetate | Tocopheryl Acetate | Roche Vitamins, Inc. | 1.60 |
| | Green Herbal Fragrance | Fragrance | Bell Flavors Fragrances | 0.30 |
| Total | — | — | — | 100.00 |

Ingredient Suppliers

International Flora Technologies

1151 N. Fiesta Boulevard
Gilbert, Arizona 85233-2238
Caschem, Inc.

40 Avenue A
Bayonne, New Jersey 07002
Strahl & Pritsch, Inc.

230 Great East Neck Road
West Babylon, New York 11704
Roche Vitamins & Fine Chemicals Division of Hoffman-La Roche, Inc.
340 Kingsland Street
Nutley, New Jersey 07110-1199
Nipa Laboratories, Inc.

3411 Silverside Road
104 Hagley Building
Wilmington, Delaware 19810
Henkel Corporation 1301 Jefferson Street
Hoboken, New Jersey 07030
International Sourcing, Inc.

121 Pleasant Avenue
Upper Saddle River, New Jersey 07458
Bell Flavors & Fragrances Inc.

500 Academy Drive
Northbrook, Illinois 60062
Chemo Iberica

C/Caleruega 102,6ᵉ
Madrid 28033
Espana
Lusochimica, S.P.A.

Via Carnia, 26
20132 Milano
Italy

Phase A of both Examples is an improved emollient phase, which may also serve as the carrier phase containing active ingredients for delivery to the selected area. Phases B and C include active ingredients, which in the preferred embodiments, are generally antioxidants, antifungals and fragrance oils. The present invention, however, may or may not contain one or more active ingredients.

The emollient composition of Examples 1 and 2 were prepared in the following manner:

1. The solid waxes of Phase A were combined and melted at 90° C. They were then cooled to 80° C and the remaining constituents of Phase A were added. This mixture was mixed with moderate agitation for 1 hour. (Miconazole nitrate will not dissolve completely into the waxes.)

2. The temperature of the Phase A constituents was maintained at 80° C. and, once the Miconazole nitrate was 90% dissolved, Phase B was added to Phase A and mixed with moderate agitation for 10 minutes to create Phase AB.

3. Phase AB was cooled to 75° C. Phase C was added to Phase AB under moderate agitation. Mixing is continued with moderate agitation for 10 minutes. The resulting product was cooled and containers were filled with finished product at 58° C.–68° C.

Active materials that may be included in the emollient composition according to the invention include, but are not limited to: antifungal products, essential oils, enzymes, antioxidants, antibacterials, vitamins (such as vitamin E, vitamin E acetate, vitamin A palmitate, beta-carotene, vitamin C, or others), hormones, proteins, herbal extracts, antimicrobial agents, analgesics, topical anesthetics, skin coloring agents (e.g., skin whitening agents such as kojic acid), sun blocks (organic or inorganic ultraviolet radiation absorbing or reflecting compounds), insect repellants, hormones, cosmeceuticals, pigments and botanical extracts. Further, any known or new types of topical treatments or active materials could be reasonably be contained within the emollient compositions of the present invention. Antifungals that can be used in the practice of the invention and suggested percentages (where established) in the emollient composition are: (1) calcium undecylenate 10–25% (individually or combined with next 2 ingredients); (2) undecylenic acid (see #1); (3) zinc undecylenate (see #1); (4) pinus pinaster bark extract; (5) PVP-Iodine 10%; (6) Vitis Vinifera (Grape) Seed Extract; (7) miconozole nitrate 2%; (8) clinoquinol 3%; (9) haloprogin 1%; (10) tolnaftate 1%; (11) tea tree oil 1.25%; and (12) ketoconozole 1%.

Other ingredients may be included in the emollient such as aesthetic materials including (1) colorants such as dyes or pigments that are generally not visible to a user after application, but merely color the emollient composition; (2) visible colorants, glitter, or UV absorbers (such as flourescent dyes) to impart color or to attract the eye of a viewer to the selected areas; and (3) fragrances (which may also be active, for example, as when used in aromatherapy). Furthermore, compatible cosmetic ingredients may be added to an emollient according to the invention to achieve different melting points, flow characteristics, water resistance, or other properties. Examples of other cosmetic ingredients which may be suitable for addition to the emollient are beeswax, castor wax, carnauba wax, vegetable oils, hydrogenated or partially hydrogenated vegetable oils, surfactants such as Tween 60T™ or Tween 80™ (polysorbate 60 and polysorbate 80), silicone preparations, alpha and beta hydroxy acids, vitamins (such as vitamin E, vitamin E acetate, vitamin A palmitate, beta carotene, vitamin C, or others), herbal extracts, alpha-bisabolol, conjugated linolenic acid (CLA), antioxidants such as tocopherols or mixed natural tocopherols, other antioxidants such as BHA or BHT.

A. Melting Point Test.

The melting point range of various product samples was determined on a Fisher Johns Melting Point apparatus, and the results are shown below:

| Product Sample | Melting Point Range |
| --- | --- |
| Chap Stick Lip Balm | 51 to 57° C. |
| Chap Stick Medicated Lip Balm | 55 to 58° C. |
| Chap Stick Lip Moisturizer | 52 to 56° C. |
| Blistex Regular | 48–53° C. |
| Lip Smacker | 51–54° C. |
| Healing Garden Lip Balm | 50 to 54° C. |
| Product According to Example 1 | 47–51° C. |

The lack of as sharp melting point for each product tested reflects the amorphous nature of the product category and is the result of each containing a variety of waxes, oils and other ingredients. Some melting begins to take place at the lowest temperature indicated and at the higher temperature of the range all appears to be melted. As can be seen, the product according to the present invention had the lowest melt temperature range of the products tested.

B. Slip-Glide or Skin Lubrication Test.

The ease of application of cosmetic products provided in "stick" form (of which the present semi-solid emollient may be provided) is known by those skilled in the art as "slip." The easier the product is to apply (i.e., the less force it takes to apply the product), the greater the "slip" of the product. The phenomenon is also described as "glide" or "skin lubrication." When manufacturing cosmetics it is desirable to create products with high skin lubricity that glide on easily and do not feel greasy after application.

To test the slip of a product according to the invention, a Chatillon DFM-10 Force Meter was used. The Chatilion Force Meter is typically used to determine the force required to break molded lipsticks. The lipstick breakage test is performed by vertically securing a molded lipstick in a horizontally moving "block" of the Force Meter. The block and lipstick are moved at a constant rate towards a horizontal probe of a Chatillon gauge. The lipstick is passed through the plane of the probe whereupon it impacts the probe and breaks. The Chatillon gauge attached to the probe registers the maximum applied compression force (kg) required to break the lipstick.

To perform the tests recorded below, a Chatillon DFM-10 Force Meter was modified by adding a "Tryon T" to the block. The Tryon T enables an operator to secure a 5 ml disposable syringe in a horizontal position on the same plane as the horizontal probe of the Chatillon gauge. The tip of each syringe opposite the plunger was cut off in order to create an open-ended syringe cavity of constant diameter. One of the below-listed product samples was poured at approximately 5 degrees above its respective melt point into each syringe. The filled syringes were allowed to solidify and temper overnight at ambient room temperature. The following day each filled tube was tested on the modified Chatillon DFM-10 Force Meter to determine the "slip" imparted by the material contained in each syringe.

During each test, the traveling block, the "Tryon T" and the syringe were moved as one unit horizontally through the plane of the probe. The probe contacted the plunger of the syringe in the manner a thumb would normally be applied in order to expel the contents of the syringe from the cavity. As the plunger of the syringe was forced through the cavity by the probe, the inner surface of the cavity was contacted by the "O" ring gaskets secured to the end of the plunger opposite the "thumb" end. The applied compression force required to push the extended plunger of the syringe through the syringe cavity was measured with the Chatillon gauge. The greater the lubricating effect or "slip" imparted by a material, the lower. the force required to push the plunger and the lower the reading recorded by the Chatillon gage.

In the first stage of the test (called a "Plug Push") an initial force was recorded as each semi solid plug of formulated product sample was expelled from the open end of the syringe cavity. After this initial test, the material that had been placed therein had lubricated the inner surface of each syringe cavity. In the second stage of the test (called a "Coated Cavity Push"), five additional readings were taken to obtain an average of the applied compression force required for each pass of the plunger though the coated cavity of each test syringe. The average force (of five readings) was recorded for each formulated product sample during the Coated Cavity Push and those values are presented below.

The product according to the invention registered the lowest force in the initial force test (Plug Push). Subsequent force readings during the Coated Cavity Push showed the formulation of the present invention again had the lowest recorded force for any Product Sample. Therefore, the "slip" imparted by the formulation according to the invention can be said to be greater than for any other formulated product sample tested.

| Product Sample | Plug Push | Coated Cavity Push |
| --- | --- | --- |
| Product According to Example 1 | 0.75 kg | 0.270 kg |
| Lip Smacker | 1.080 kg | 0.330 kg |
| Healing Garden | 0.915 kg | 0.375 kg |
| Chap Stick Lip Balm | 2.170 kg | 0.465 kg |
| Blistex Regular | 1.095 kg | 0.55 kg |
| Chap Stick Medicated | 3.265 kg | 1.130 kg |
| Chap Stick Lip Moisturizer | 3.235 kg | 1.245 kg |

The container used to retain the emollient can be of any type that (1) is convenient to carry (i.e., it can fit into a purse or pocket), and (2) enables a user to apply the emollient to a selected area without requiring the use of fingers to contact the solid to semi-solid emollient during application. Any container that satisfies these conditions may be used. Such a container may be of any shape and could be formed of any material. For example, the container could be a pencil, similar to a wax pencil or eyeliner pencil. The semi-solid nature of the improved emollient prevents migration of the emollient from areas selected for treatment to unselected areas of the fingers or toes or to clothing, furniture or other unselected surfaces. The container enables the user to deliver the emollient cuticle treatment to preferably only the selected area and thereby enhance the dry emollient feel at the selected surface.

Figure 2:
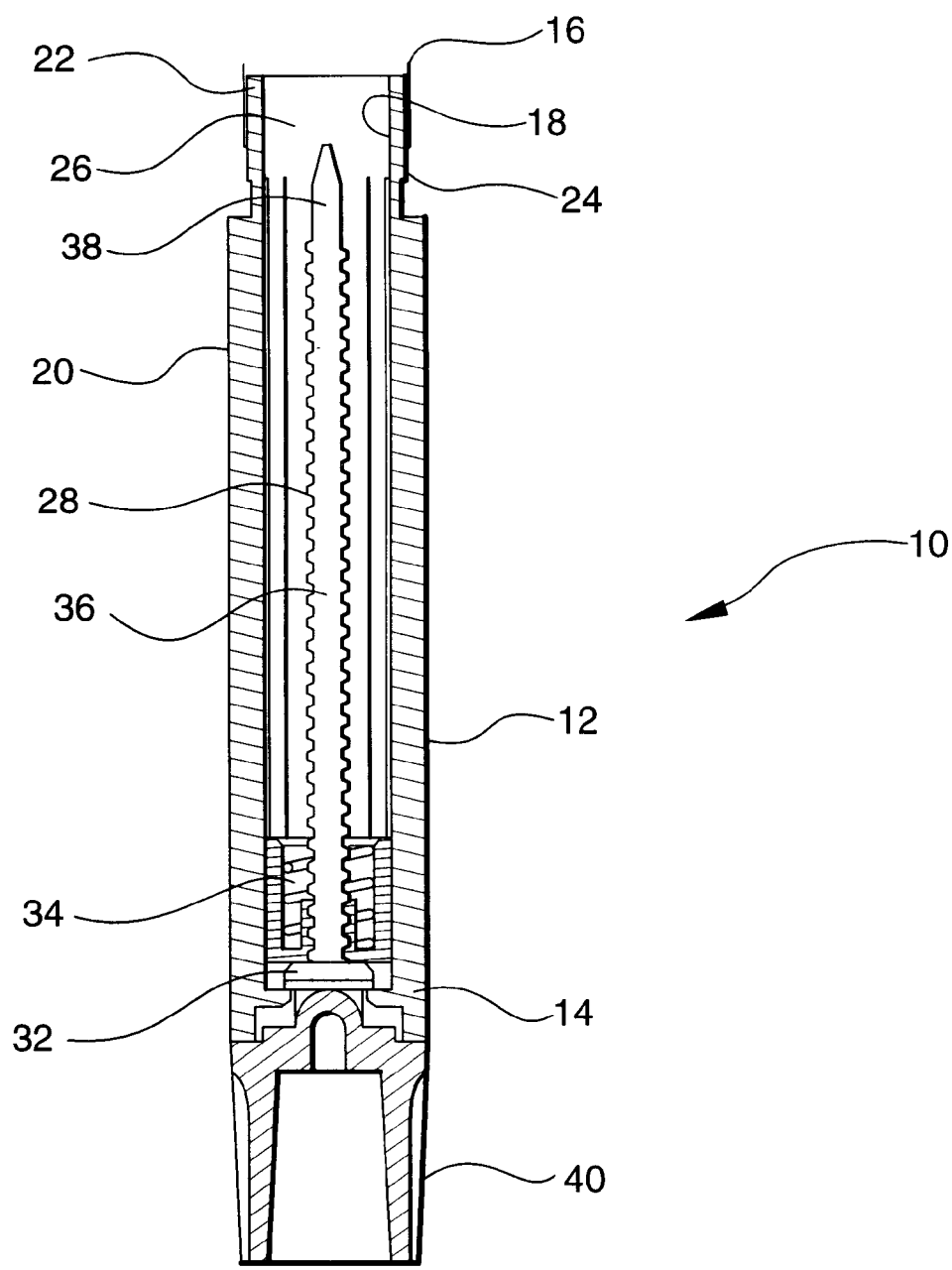
FIG. 2 is a cross-sectional view of the container of FIG. 1.

The preferred container 10 is illustrated in FIGS. 1 and 2 and is preferably a Slimline® repel-propel container manufactured by Federal Packaging Inc. 4044 Peavey Road, Chaska, Minn. 55318. Container 10, as well as mechanism 28, thumbscrew 40 and cap 44, which will be described in greater detail below, are preferably made of any suitable plastic, although each can be made of any other suitable material, such as metal. Turning now to FIG. 1, container 10 preferably has a tubular body 12 having a first end 14 and a second end 16. Body 12 has a length of approximately 2.3" and includes (1) a cylindrical inner wall 18, which has a preferred diameter of approximately 0.350" and extends the entire length of tube 12, (2) a cylindrical outer wall 20, having a preferred diameter of approximately 0.460" and a preferred length of approximately 1.925", and (3) a recessed section at second end 16 defined by inner wall 18 and cylindrical outer wall 22, which has a preferred diameter of approximately 0.380" and a preferred length of approximately 2.3". An annular lip (also called a snap bead) 24 is formed on wall 22 and has a diameter slightly greater than that of wall 22.

A cavity 26 is defined within body 12. There is retained within cavity 26 a propel-repel mechanism 28 for extending and retracting a semi-solid emollient. Preferably, mechanism 28 includes a base 32, a threaded retainer 34 and a threaded rod 36. Threaded rod 36 has a tapered, non-threaded end 38 opposite retainer 34. As shown in FIG. 2, base 32 is connected to the bottom of retainer 34 and threaded rod 36 is received in retainer 34.

A thumbscrew 40 is attached to first end 14, and connected to base 32. Thumbscrew 40 is preferably tapered and has an outer diameter equal to the diameter of wall 18 at the end where it connects to tube 12 and an outer diameter of 0.40" at the opposite end. Thumbscrew 40 includes a plurality of indentations 42, which are preferably radially spaced about its periphery, and are for the purpose of providing the user a better grip.

Figure 3:
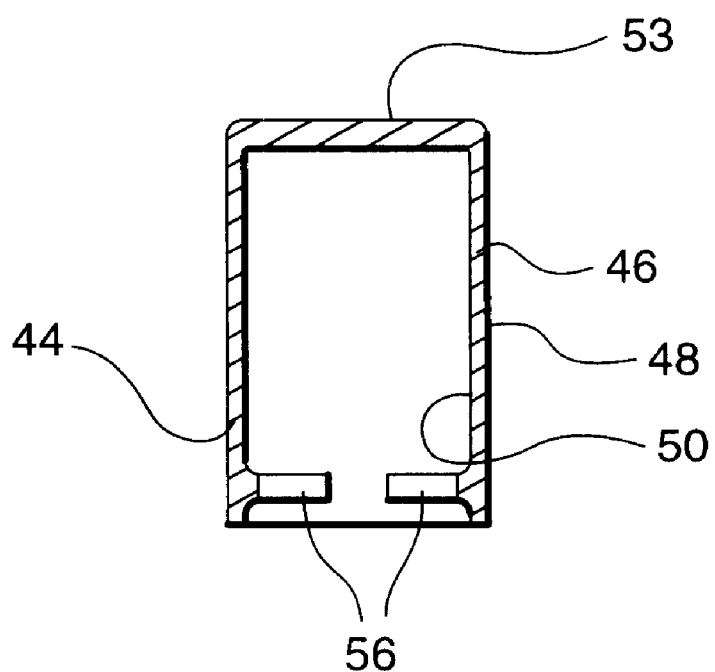
FIG. 3 is a cross-sectional view of the cap of FIG. 1.

A preferred cap 44 is shown in FIGS. 1 and 3. Cap 44 has a cylindrical wall 46 including an outer wall 48 and an inner wall 50, wherein inner wall 50 defines a cavity 52. Cap 44 also includes a top wall 53 and an annular projection 56 that extends from inner wall 50 into cavity 52. Projection 56 is for retaining cap 44 on second end 16 of container 10 and it is positioned such that it is retained by annular lip 24 when cap 44 is pressed onto end 16.

In operation, an emollient is placed within cavity 26 and cap 44 is pressed onto end 16. When used, cap 44 is removed and thumbscrew 40 is turned in one direction, turning base 32 and rod 36, which turns the threads of rod 36 within the threads of retainer 34. This moves retainer 34 towards second end 16 and retainer 34 pushes (or extends) the emollient retained within cavity 26 out of the opening at second end 16, thereby exposing it for use. When thumbscrew 40 is turned in the opposite direction, rod 34 turns in that direction and retainer 34 moves towards first end 14 and the emollient preferably retracts into cavity 26.

Packaging a cuticle care formulation containing semi-solid emollients, particularly emollients with a "dry" feel, in a container, such as an extendable/retractable container, allows the emollient to be portable and easily used. This precise delivery of the emollient, due to the container and/or the semi-solid form of the emollient, helps to reduce the greasy feeling experienced when consumers apply other cuticle treatment products or have them applied by others, such as during a visit to a nail salon. A further advantage of the use of a container according to the invention is that it makes the emollient available for use at any time, and it can be used at virtually any time because the emollient is applied only to the cuticles and does not get on the user's fingertips. Thus, the emollient can be used in everyday home or office situations or in the evening during leisure time with little risk of contacting unselected surfaces with greasy or staining materials.

Another embodiment for a container is a pencil type tube. The interior of tube is hollow to contain the emollient. Thus, one needs only to "sharpen" the "pencil" or remove a portion of the tube container to project a portion of the contained emollient therefrom. Once the semi-solid emollient projects from the tube, the user may apply it onto selected areas. Another version of this same pencil type container is a "wrapped" pencil or one where the outer container is a continuous ribbon of material such as a stiff paper. The ribbon is wrapped about a stick of semi-solid emollient to conveniently package and contain the emollient. Thus, in this embodiment, the use need only unwrap a portion of the end of the wrap type pencil to project a portion of the contained emollient stick. As above, once the semi-solid emollient projects from the tube, the user may apply it onto selected areas.

The preferred embodiment of the invention is described above in the Drawings and Description of Preferred Embodiments. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s). The foregoing description of a preferred embodiment and best mode of the invention known to the applicant at the time of filing the application has been presented and is intended for the purposes of illustration and description. It is not intended to be exhaustive or to limit the invention to the precise form disclosed, and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated.

What is claimed is:

1. A semi-solid emollient composition for cuticle treatment.

2. The semi-solid emollient composition of claim 1 wherein the composition has a melt temperature ranging between 40–60 degrees Celcius.

3. The semi-solid emollient composition of claim 2 wherein the composition further has a melt temperature ranging between 47–51 degrees Celsius.

4. The product of claim 2 wherein the semi-solid emollient composition imparts a dry feel to the user.

5. The product of claim 2 wherein the semi-solid emollient composition for cuticle treatment comprises esterified materials derived from natural seed and/or nut oils.

6. The product of claim 5 wherein the esterified natural organic oils are jojoba esters.

7. The emollient of claim 5 wherein the esterified natural organic oils are saturated and/or unsaturated ethyl esters and/or isopropyl esters of (a) long-chain fatty acids, and/or (b) alcohols, wherein the long-chain fatty acids and alcohols are derived from plant seed oils.

8. The semi-solid emollient composition of claim 2 that further includes one or more active ingredients.

9. The semi-solid emollient composition of claim 8 wherein the one or more active ingredients is selected from the group consisting of antifungals, colorants, fragrances, antimicrobial agents, analgesics, topical anesthetics, skin whitening agents, sun blocks, insect repellants, vitamins, hormones, proteins, cosmeceuticals, and botanical extracts.

10. A product for treating cuticles with emollient, the product comprising:

(a) a semi-solid emollient composition for cuticle treatment; and (b) a container that retains the semi-solid emollient and enables a user to apply the emollient to a selected surface without the user having to touch the emollient with his/her finger tips.

11. The semi-solid emollient composition of claim 10 wherein the composition has a melt temperature ranging between 40–60 degrees Celcius.

12. The semi-solid emollient composition of claim 11 wherein the composition further has a melt temperature ranging between 47–51 degrees Celsius.

13. The product of claim 11 wherein the semi-solid emollient composition imparts a dry feel to the user.

14. The product of claim 11 wherein the semi-solid emollient composition for cuticle treatment comprises esterified materials derived from natural seed and/or nut oils.

15. The product of claim 14 wherein the esterified natural organic oils are jojoba esters.

16. The emollient of claim 14 wherein the esterified natural organic oils are saturated and/or unsaturated ethyl esters and/or isopropyl esters of (a) long-chain fatty acids, and/or (b) alcohols, wherein the long-chain fatty acids and alcohols are derived from plant seed oils.

17. The product of claim 11 wherein the emollient further comprises one or more active ingredients.

18. The product of claim 17 wherein the one or more active ingredients is selected from the group consisting of antifungals, colorants, fragrances, antimicrobial agents, analgesics, topical anesthetics, skin whitening agents, sun blocks, insect repellants, vitamins, hormones, proteins, cosmeceuticals, and botanical extracts.

19. The product of claim 11 wherein the container has an opening and includes a removable cap that covers the opening.

20. The product of claim 19 wherein the container is a pencil form.

21. The product of claim 20 wherein the pencil form container is less than 10" in length.

22. The product of claim 11 wherein the container is a propel/repel container that includes a device for extending the semi-solid emollient composition retained therein.

23. The product of claim 22 wherein the container has an opening and includes a removable cap that covers the opening, the emollient capable of being extended through the opening.

24. A method for treating a cuticle using a semi-solid emollient composition comprising the steps of providing a semi-solid emollient composition in a container and applying the semi-solid emollient composition on a selected area without touching the semi-solid emollient composition with any fingertips.

25. The method of claim 24 further comprising the step of extending the semi-solid emollient composition past an opening in the container before the step of applying the semi-solid emollient composition on a selected area.

26. The method of claim 25 wherein the step of extending the semi-solid emollient composition past an opening in the container is the step of extruding the semi-solid emollient composition past the opening in the container.

27. The method of claim 25 wherein the step of extending the semi-solid emollient composition past an opening in the container is the step of removing portions of the container, thereby leaving a portion of the semi-solid emollient composition behind and extending past a remaining portion of the container.

28. The method of claim 24 further comprising the step of removing a cap from the container of the semi-solid emollient composition before the step of applying the semi-solid emollient composition on a selected area.

29. The method of claim 28 further comprising the step of replacing the cap on the container after the step of applying the semi-solid emollient composition on a selected area.

30. The method of claim 24 further comprising the steps of removing a cap from the container of the semi-solid emollient composition before the step of applying the semi-solid emollient composition, extending the semi-solid emollient composition past an opening in the container before the step of applying the semi-solid emollient composition on a selected area, wherein the step of extending the semi-solid emollient composition past an opening in the container is the step of extruding the semi-solid emollient composition past the opening in the container, and replacing the cap on the container after the step of applying the semi-solid emollient composition on a selected area.

31. The method of claim 24 further comprising the steps of removing a cap from the container of the semi-solid emollient composition before the step of applying the semi-solid emollient composition on a selected are, extending the semi-solid emollient composition past an opening in the container before the step of applying the semi-solid emollient composition, wherein the step of extending the semi-solid emollient composition past an opening in the container is the step of removing portions of the container, thereby leaving a portion of the semi-solid emollient composition behind and extending past a remaining portion of the container, and replacing the cap on the container after the step of applying the semi-solid emollient composition on a selected area.

* * * * *